United States Patent
Fujita et al.

(10) Patent No.: US 7,364,698 B2
(45) Date of Patent: Apr. 29, 2008

(54) AUTOMATIC ANALYZER

(75) Inventors: Takehiro Fujita, Hitachinaka (JP); Katsuaki Takahashi, Hitachinaka (JP); Masaharu Nishida, Hitachinaka (JP)

(73) Assignees: Hitachi High-Technologies Corporation, Tokyo (JP); Hitachi Science Systems, Ltd., Hitachinaka-shi (JP)

( * ) Notice: Subject to any disclaimer, the term of this patent is extended or adjusted under 35 U.S.C. 154(b) by 809 days.

(21) Appl. No.: 10/756,511

(22) Filed: Jan. 14, 2004

(65) Prior Publication Data
US 2004/0185549 A1 Sep. 23, 2004

(30) Foreign Application Priority Data
Mar. 18, 2003 (JP) .............................. 2003-073118

(51) Int. Cl.
*G01N 21/13* (2006.01)
*B01L 3/02* (2006.01)

(52) U.S. Cl. ........................................ 422/63; 422/100
(58) Field of Classification Search ................ 422/63, 422/100
See application file for complete search history.

(56) References Cited

U.S. PATENT DOCUMENTS 5,736,100 A 4/1998 Miyake et al. ................ 422/64
6,593,090 B2* 7/2003 Connolly ........................ 435/6
6,793,890 B2* 9/2004 Morales et al. ............... 422/99
7,229,592 B2* 6/2007 Devlin et al. .................. 422/67
2003/0203491 A1* 10/2003 Andrevski et al. ............ 436/46
2004/0115095 A1* 6/2004 Devlin et al. .................. 422/63

FOREIGN PATENT DOCUMENTS

| JP | 08-146007 | 6/1996 |
|---|---|---|
| JP | 08-201397 | 8/1996 |
| JP | 2001-242177 | 9/2001 |

* cited by examiner

*Primary Examiner*—Brian R Gordon
(74) *Attorney, Agent, or Firm*—Mattingly, Stanger, Malur & Brundidge, P.C.

(57) ABSTRACT

Without causing an increase in size and complication of an automatic analyzer, the efficiency of washing cuvettes can be increased and the amount of detergent used can be more effectively saved in comparison with known analyzers. In an automatic analyzer in which a sample and a reagent are dispensed into each of a plurality of cuvettes, a resulting reaction solution is mixed under stirring, and reaction states of the mixed reaction solution are measured successively. The automatic analyzer includes a unit for stirring a detergent in the cuvette when the interior of the cuvette is washed with the detergent after measurement of a reaction. The automatic analyzer also includes a control device controlling steps of reaction measurement and washing and incorporating a sequence of stirring in the washing step. A mixing unit for mixing the reaction solution also serves as the unit for stirring the detergent in the cuvette.

1 Claim, 2 Drawing Sheets

FIG.2

DISPENSING OF SAMPLE
(1ST CYCLE)

STIRRING OF REACTION SOLUTION
(2ND CYCLE)

SUCTION OF REACTION SOLUTION +
POURING OF DETERGENT (10TH CYCLE)

SUCTION OF REACTION SOLUTION +
POURING OF PURE WATER (11TH CYCLE)

DRYING
(12TH CYCLE)

DISPENSING OF REAGEN
(1ST CYCLE)

STIRRING OF DETERGENT
(10TH CYCLE)

STOP A — 4-PITCH ROTATION — STOP B — 9-PITCH ROTATION

1 CYCLE

AUTOMATIC ANALYZER

BACKGROUND OF THE INVENTION

1. Field of the Invention

The present invention relates to an analyzer for analyzing ingredients contained in a sample, such as blood and urine, and more particularly to an automatic analyzer of the type washing a cuvette to be used again.

2. Description of the Related Art

There is known an automatic analyzer in which a sample and a reagent are dispensed into each of a plurality of cuvettes, a resulting reaction solution is mixed under stirring, and reaction states of the mixed reaction solution are measured successively. A mechanism for mixing the reaction solution during the measurement has been practiced with a method of inserting a spatula into the cuvette and rotating the spatula to stir the reaction solution, or a method of irradiating an ultrasonic wave to the cuvette from the outside for stirring the reaction solution in the cuvette (shown in JP,A 2001-242177).

On the other hand, a method of washing the cuvette with a detergent after the measurement of reaction occurred in the reaction solution is usually practiced by sucking and discarding the reaction solution after the end of the measurement, followed by repeating the steps of pouring the detergent into the emptied cuvette, sucking the poured detergent, and then discarding it several times.

SUMMARY OF THE INVENTION

However, the method of repeating the steps of simply pouring the detergent into the cuvette and discarding it from the cuvette is disadvantageous in points given below. The washing efficiency is poor in removing contaminants attached to an inner wall of the cuvette, and the steps of pouring the detergent and discarding it must be repeated in an increased number of times. In order to clean the interior of the cuvette by degrees, the number of detergent pouring valves and the number of detergent discarding valves must be increased correspondingly. This leads to not only an increase in size and complexity of the analyzer, but also the necessity of using a larger amount of detergent.

Accordingly, it is an object of the present invention to provide an automatic analyzer in which, without causing an increase in size and complexity of the analyzer, the efficiency of cuvette washing can be increased and the amount of detergent used can be more effectively saved in comparison with known automatic analyzer.

The above object is achieved, according to the present invention, with an automatic analyzer in which a sample and a reagent are disposed into each of a plurality of cuvettes, a resulting reaction solution is mixed under stirring, and reaction states of the mixed reaction solution are measured successively, wherein the automatic analyzer includes a unit for stirring a detergent in the cuvette when the interior of the cuvette is washed with the detergent after measurement of a reaction occurred in the reaction solution. In other words, the above object is achieved with an automatic analyzer of the above-mentioned type, wherein the automatic analyzer includes a control device having control sequence for stirring the detergent in the washing step during the reaction measurement and washing step.

BRIEF DESCRIPTION OF THE DRAWINGS

FIG. 2 is a time chart showing movement of a reaction disk shown in FIG. 1.

DESCRIPTION OF THE PREFERRED EMBODIMENTS

Figure 1:
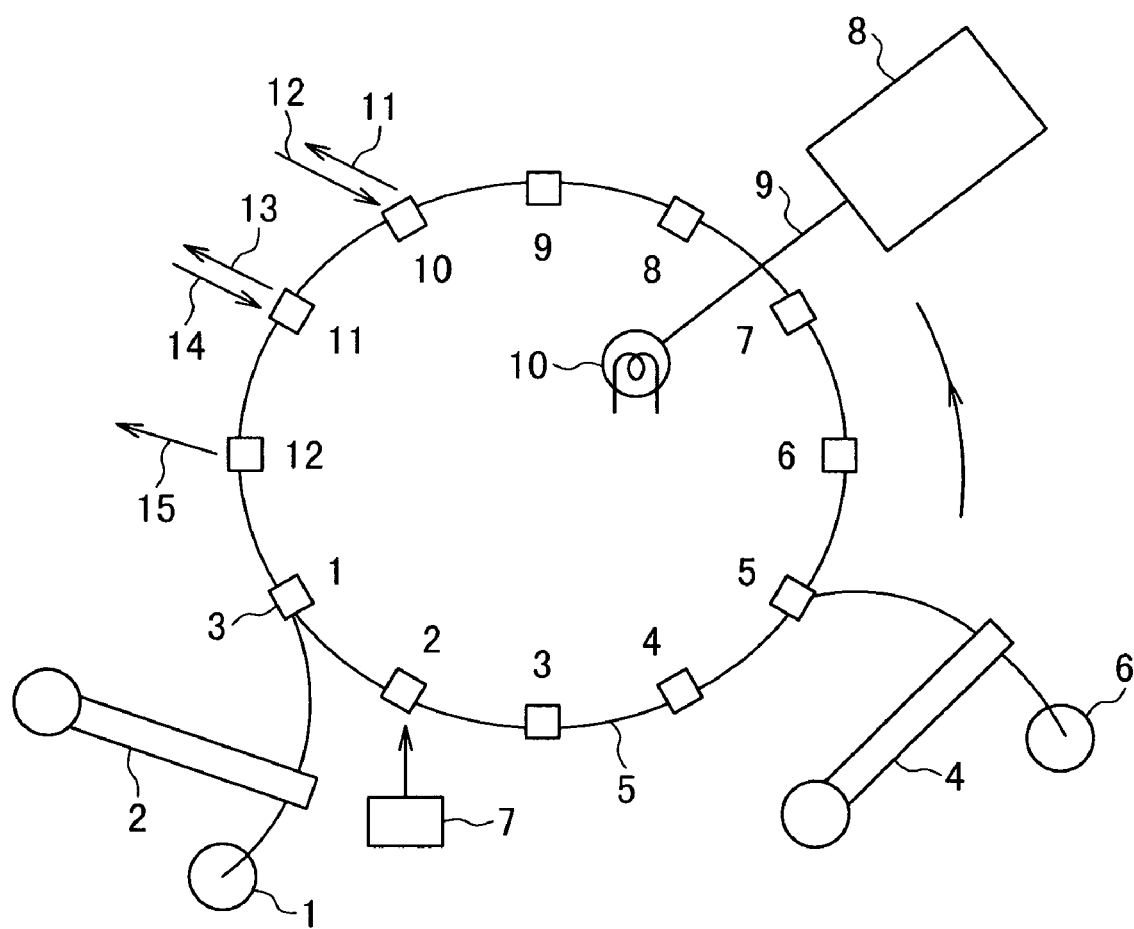
FIG. 1 is a schematic view for explaining an automatic analyzer to which the present invention is applied.

An embodiment of the present invention will be described below with reference to FIGS. 1 and 2.

FIG. 1 shows the construction of an automatic analyzer of this embodiment. In the illustrated embodiment, for the simplicity of explanation, the analyzer includes a turntable on which 12 cuvettes are arranged in the circular form. Particularly, the analyzer employs an ultrasonic oscillator for mixing a reaction solution. With attention focused on movement of one cuvette (A) denoted by numeral 3, the following description is made while tracking the movement sequence of the cuvette (A). Each of numbers put along the circumference of a reaction disk 5 denotes a position where the cuvette is stopped.

A sample in a sample cup 1 is dispensed into the cuvette (A) by using a sample sampling mechanism 2. Then, the reaction disk 5 is rotated through 4 pitches and stopped. In this state, the cuvette (A) is stopped in a position No. 5 where a reagent in a reagent bottle 6 is dispensed into the cuvette (A) by using a reagent sampling mechanism 4. Then, the reaction disk 5 is rotated through 9 pitches and stopped. In this state, the cuvette (A) is stopped in a position No. 2. An ultrasonic mixing device 7 is actuated to irradiate an ultrasonic wave to the cuvette (A). A reaction solution (i.e., a mixed solution of the sample and the reagent) in the cuvette (A) is thereby stirred for mixing so that a reaction starts in the reaction solution. Each time the cuvette crosses a light pass 9 of a photometer 8, the absorbance of the reaction solution in the cuvette is measured to detect the state of progress of the reaction. In such a manner, quantitative analysis of an ingredient contained in the sample is carried out.

One cycle of the movement of the cuvette proceeds in accordance with a time chart shown in FIG. 2. As shown in FIG. 2, one cycle is made up of a 4-pitch rotation, a stop, a 9-pitch rotation, and a stop. In other words, during one cycle, the reaction disk 5 is rotated through one rotation and one pitch. Eventually, the reaction disk 5 is advanced one pitch per cycle.

After repeating the above-described operation through further 8 cycles, the cuvette (A) is stopped at a position No. 10 and the analysis is completed. Subsequently, the reaction solution is sucked by a sucking nozzle 11, and a detergent is poured into the cuvette (A) by a detergent pouring nozzle 12. The cuvette (A) containing the detergent is then stopped so as to position in front of the ultrasonic mixing device 7 at the timing of a "stop B" in the time chart. In this state, the ultrasonic mixing device 7 is actuated to irradiate an ultrasonic wave to the cuvette (A). The ultrasonic wave agitates the detergent in the cuvette (A) to remove dirt adhering to an inner wall of the cuvette (A). It is well known that ultrasonic washing has a great effect in removing dirt. The ultrasonic washing is particularly effective in removing dirt from all corners. The ultrasonic mixing device is capable of not only irradiating an ultrasonic wave that is strong enough to agitate the reaction solution for the purpose of stirring, but also enabling vibrations of the ultrasonic wave to spread up to every nook and corner of the cuvette (A). Thus, the use of such an ultrasonic mixing device provides a great washing effect. After removing dirt from every nook and corner of the cuvette (A), the detergent is sucked by a sucking nozzle 13, and pure water is poured into the cuvette (A) from a pure water pouring nozzle 14 to rinse the interior of the cuvette (A). After drying the interior of the cuvette in a next cycle by a drying nozzle 15, the cuvette (A) is used again for new analysis.

Thus, with this embodiment, the steps of washing and drying the interior of the cuvette are carried out in three stages, i.e., in the positions Nos. 10, 11 and 12, by using a relatively small number of nozzles.

The above embodiment has been described in connection with the case in which a mixing unit for mixing the reaction solution under stirring to promote the reaction serves also as a stirring unit for stirring the detergent in the cuvette for the purpose of reducing the product cost. However, an additional unit for dedicatedly stirring the detergent in the cuvette may be separately provided. This modification is able to simplify the sequence control.

Also, the above embodiment has been described in connection with the case of using an ultrasonic oscillator as means for stirring (or mixing) the liquid in the cuvette. As an alternative, however, it is also possible to employ a method of using an inexpensive stirrer (e.g., a spatula) to stir the liquid in the cuvette, or a method of spraying air bubbles to stir the liquid in the cuvette.

Further, by inserting, in the cuvette, a chip made of a material, e.g., Teflon, which does not damage the inner wall of the cuvette during the stirring of the detergent, a level of the detergent in the cuvette rises upon insertion of the chip and hence the amount of detergent used can be reduced correspondingly.

According to the present invention, as described above, in an automatic analyzer in which a sample and a reagent are pipetted into each of a plurality of cuvettes, a resulting reaction solution is mixed under stirring, and reaction states of the mixed reaction solution are measured successively, the automatic analyzer includes a unit for stirring a detergent in the cuvette when the interior of the cuvette is washed with the detergent after measurement of a reaction occurred in the reaction solution. Stated another way, in an automatic analyzer of the above-mentioned type, the automatic analyzer includes a control device controlling steps of reaction measurement and washing carried out in the automatic analyzer and incorporating a sequence of stirring in the washing step. With the automatic analyzer, without causing an increase in size and complication of the analyzer, the efficiency of washing cuvettes used in the analyzer can be increased and the amount of detergent used can be more effectively saved in comparison with known analyzers.

What is claimed is:

1. An automatic analyzer arranged for dispensing a sample and a reagent into a cuvette, stirring and mixing a reaction solution of said sample and reagent in the cuvette, and measuring for analysis the reaction states of said reaction solution, said automatic analyzer comprising:

dispensing means for dispensing the sample and the reagent into the cuvette, thereby forming the-reaction solution in the cuvette;

an ultrasonic mixing device arranged at one fixed position in the automatic analyzer, said ultrasonic mixing device being arranged to mix the reaction solution in the cuvette a measurement device arranged to measure for analysis the reaction states of the reaction solution in the cuvette; and a detergent pouring means for pouring a detergent into the cuvette after measurement by the measurement device;

wherein the ultrasonic mixing device is further arranged to agitate the detergent in the cuvette, such that said mixing of the reaction solution in the cuvette and said agitating of the detergent in the cuvette are both performed by said ultrasonic mixing device at said one fixed position in the automatic analyzer; and a control device arranged to implement a control sequence, including controlling steps of dispensing the sample into the cuvette, dispensing the reagent into the cuvette, mixing the reaction solution in the cuvette, measuring the reaction states of the mixed reaction solution in the cuvette, removing the reaction solution from the cuvette, pouring the detergent into the cuvette, and agitating the detergent in the cuvette, wherein the steps of mixing the reaction solution in the cuvette and agitating the detergent in the cuvette are both performed at said one fixed position in the automatic analyzer.

* * * * *